(12) United States Patent
Yelle

(10) Patent No.: US 6,342,488 B1
(45) Date of Patent: Jan. 29, 2002

(54) PHOSPHONORISPERIDONE AND SULFORISPERIDONE COMPOSITIONS AND METHODS

(75) Inventor: William E. Yelle, Littleton, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/762,968

(22) PCT Filed: Aug. 17, 1999

(86) PCT No.: PCT/US99/18631

§ 371 Date: Feb. 15, 2001

§ 102(e) Date: Feb. 15, 2001

(87) PCT Pub. No.: WO00/10572

PCT Pub. Date: Mar. 2, 2000

Related U.S. Application Data
(60) Provisional application No. 60/097,004, filed on Aug. 18, 1998, and provisional application No. 60/113,118, filed on Dec. 21, 1998.

(51) Int. Cl.⁷ .................... A61K 31/675; A61K 31/505
(52) U.S. Cl. .......................................... 514/80; 514/258
(58) Field of Search ................... 514/80, 258

(56) References Cited

U.S. PATENT DOCUMENTS
5,158,952 A 10/1992 Janssen et al. .............. 514/258

FOREIGN PATENT DOCUMENTS
| | | |
|---|---|---|
| EP | 0 368 388 | 5/1990 |
| WO | WO 97/44039 | 11/1997 |

OTHER PUBLICATIONS
Megens et al., "In Vivo Pharmacological Profile of 9–Hydroxyrisperidone, the Major Metabolite of the Novel Antipsychotic Risperidone," *Drug Devel Res*, 33:399–412 (1994).

Lalith, Misra et al., "Risperidone Treatment of Methamphetamine Psychosis," *Am J Psychiatry*, 154:1170 (Aug. 1997).

Smelson, David et al., "Risperidone Diminishes Cue–Elicited Craving in Withdrawn cocaine–Dependent Patients," *Can J Psychiatry*, 42:984 (Nov. 1997).

*Primary Examiner*—William R. A. Jarvis
(74) *Attorney, Agent, or Firm*—Heslin Rothenberg Farley & Mesiti P.C.

(57) ABSTRACT

Methods and compositions utilizing compounds represented by Formula III,

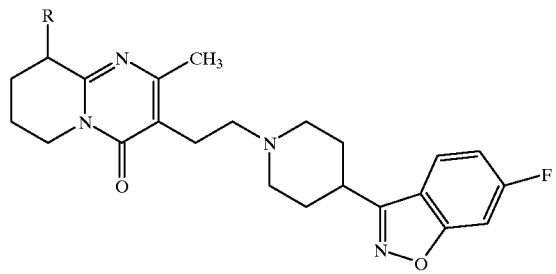

III wherein R is chosen from —P(O)(OH)$_2$ and —SO$_3$H, or pharmaceutically acceptable salts thereof, for the treatment and prevention of psychoses in humans are disclosed. Compounds of the present invention exhibit fewer side effects than risperidone, a lessened liability toward drug-drug interactions than risperidone and a more predictable dosing regimen than risperidone. Compounds of the invention are also useful for the treatment and prevention of emesis and withdrawal syndromes.

18 Claims, No Drawings

PHOSPHONORISPERIDONE AND SULFORISPERIDONE COMPOSITIONS AND METHODS

CROSS REFERENCE TO RELATED APPLICATIONS

This application is a §371 filing of International Application PCT/US99/18631, filed Aug. 17, 1999, and claims priority from U.S. Provisional Application No. 60/097,004 filed Aug. 18, 1998 and No. 60/113,118 filed Dec. 21, 1998. The entire disclosures of the earlier applications are incorporated herein by reference.

FIELD OF THE INVENTION

This invention relates to compositions of matter containing hydroxyrisperidone. The invention also relates to methods of treating and preventing psychoses, emesis and symptoms of withdrawal from alcohol and nicotine.

BACKGROUND OF THE INVENTION

Risperidone I is an orally active, potent antipsychotic agent commercially available in the form of Risperidal® tablets and oral solution from Janssen Pharmaceutica.

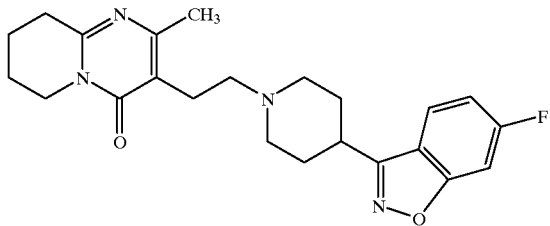

I

The $C_{max}$ of risperidone in humans is at about 3 to 9 hours after oral administration, and the serum half-life is about 2 to 22 hours; both of these parameters are highly variable, depending on the subject's age, liver function, and CYP 2D6 phenotype, as will be discussed below. The major metabolite in human serum is 9-hydroxyrisperidone II (hereinafter, "hydroxyrisperidone").

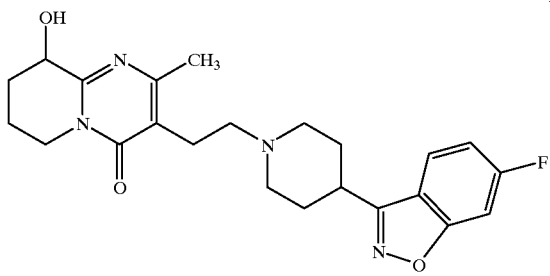

II

The hydroxylation of risperidone to its active metabolite, hydroxyrisperidone, is catalyzed in vivo by the hepatic cytochrome P450 enzyme, CYP2D6, an enzyme that is involved in the metabolism of numerous other drugs, including tricyclic antidepressants and selective serotonin reuptake inhibitors. CYP2D6 is polymorphically expressed in the human population and the mutant allele constitutes the recessive trait. Homozygous carriers of the mutation completely lack CYP2D6 and are referred to as poor metabolizers (PM's); persons homozygous for the "normal" allele are extensive metabolizers (EM's); heterozygotes appear to be intermediate in metabolic capacity.

It would be desirable to find a compound that has the advantages of risperidone while providing a more predictable dosage regimen in the patient population and decreasing the chances for drug-drug interactions.

Risperidone is known to give rise to several side effects, and in particular, to extrapyramidal effects such as tardive dyskinesia. The most frequently observed adverse reactions include orthostatic hypotension and dizziness, drowsiness, palpitations, weight gain, erectile dysfunction, and a significant increase in rashes and rhinitis.

The following adverse events have been reported in risperidone-treated patients:

Psychiatric disorders—insomnia, agitation, anxiety, somnolence, aggressive reaction, increased dream activity, diminished desire, nervousness, depression, apathy, catatonic reaction, euphoria, increased libido, amnesia, emotional lability, nightmares, delirium, withdrawal syndrome, yawning.

Central and Peripheral Nervous system disorders—extrapyramidal symptoms (including tremor, dystonia, hypokinesia, hypertonia, hyperkinesia, oculogyric crisis, ataxia, abnormal gait, involuntary muscle contractions, hyporeflexia, akathisia, increased sleep duration, dysarthria, vertigo, stupor, paraesthesia, confusion, aphasia, cholinergic syndrome, hypoesthesia, tongue paralysis, leg cramps, torticollis, hypotonia, coma, migraine, hyperreflexia and choreoathetosis.

Gastrointestinal system disorders—constipation, nausea, dyspepsia, vomiting abdominal pain, increased salivation, anorexia, toothache, reduced salivation, flatulence, diarrhea, increased appetite, stomatitis, melena, dysphagia, hemorrhoids, gastritis, fecal incontinence, eructation, gastroesophageal reflux, gastroenteritis, esophagitis, tongue discoloration, cholelithiasis, tongue edema, diverticulitis, gingivitis, discolored feces, GI hemorrhage, hematemesis Body as a whole/General disorders—back pain, chest pain, fever, fatigue, edema, rigors, malaise, influenza-like symptoms, pallor, enlarged abdomen, allergic reaction, ascites, sarcoidosis, flushing Respiratory system—rhinitis, coughing, sinusitis, pharyngitis, dyspnea, hyperventilation, bronchospasm, pneumonia, stridor, asthma, increased sputum, aspiration Dermatological—rash, dry skin, seborrhea, increased pigmentation, photosensitivity, increased sweating, acne, decreased sweating, alopecia, hyperkeratosis, pruritus, skin exfoliation, bullous eruption, skin ulceration, aggravated psoriasis, furunculosis, verruca, dermatitis lichenoid, hypertrichosis, genital pruritus, and urticaria.

Vision Disorders—abnormal accommodation, xerophthalmia, diplopia, eye pain, blepharitis, photopsia, photophobia, and abnormal lacrimation.

Metabolic and Nutritional Disorders—hyponatremia, weight increase, creatine phosphokinase increase, thirst, weight decrease, diabetes mellitus, decreased serum iron, cachexia, dehydration, hypokalemia, hypoproteinemia, hyperphosphatenia, hypertriglyceridemia, hyperuricemia, and hypoglycemia.

Urinary System Disorders—polyuria/polydipsia, urinary incontinence, hematuria, dysuria, urinary retention, cystitis, and renal insufficiency.

Musculo-Skeletal Disorders—arthralgia, myalgia, arthrosis, synostosis, bursitis, arthritis, and skeletal pain.

Reproductive Disorders—(Female) menorrhagia, orgastic dysfunction, dry vagina, nonpuerperal lactation, amenorrhea, female breast pain, leukorrhea, vaginal hemorrhage, dysmenorrhea, femal perineal pain, mastitis, and intermenstrual bleeding; (Male) erectile dysfunction and ejaculation failure.

Liver and Biliary System Disorders—increased SGOT, increased SGPT, hepatic failure, cholestatic hepatitis, cholecystitis, cholelithiasis, hepatitis, and hepatocellular damage.

Endocrine Disorders—gynecomastia, male breast pain, and antidiuretic hormone disorder.

White Cell and Resistance Disorders—leukocytosis, lymphadenopathy, leucopenia, and Pelger-Huet anomaly.

Red Blood Cell Disorders—anemia, hypochromic anemia, and normocytic anemia.

Platelet, Bleeding and Clotting Disorders—epistaxis, purpura, hemorrhage, superficial phlebitis, thrombophlebitis, and thrombocytopenia.

Hearing and Vestibular Disorders—tinnitus, hyperacusis, and decreased hearing.

Cardiovascular—tachycardia, orthostatic hypotension, palpitation, hypertension, AV block, myocardial infarction, ventricular tachycardia, angina pectoris, premature atrial contractions, T wave inversions, ventricular extrasystoles, ST depression, myocarditis, angioedema, atrial fibrillation, pulmonary embolism and cardiopulmonary arrest.

Risperidone and hydroxyrisperidone have also been implicated in a prolongation of QT interval, a condition associated with torsades de pointes, a life-threatening arrhythmia.

Accordingly, an antipsychotic having the efficacy of risperidone, but causing fewer side effects, would be desirable.

SUMMARY OF THE INVENTION

Compounds used in the methods and compositions of the present invention are represented by Formula III,

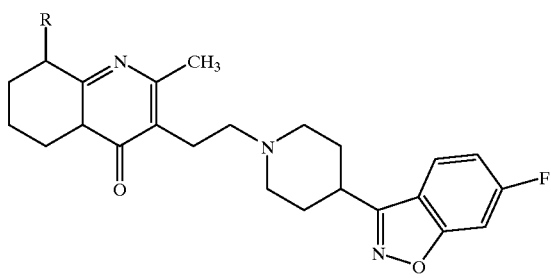

III wherein R is chosen from —OH, —P(O)(OH)$_2$ and —SO$_3$H, or a pharmaceutically acceptable salt thereof. The compounds possess potent activity in the treatment of psychotic disorders (e.g., schizophrenia) and other conditions, including those that would benefit from an antidiarrheal, an inhibitor of gastro-esophageal reflux and/or an antiemetic, especially in cancer patients receiving chemotherapy and radiation. Compounds of Formula III may also be used in combating autism, hypertension, vascular disorders, obesity, and the withdrawal symptoms associated with cessation of drinking and smoking. Compounds of Formula III provide a more predictable dosage regimen in the patient population and decrease the chances for drug-drug interactions by avoiding oxidative metabolism for which the cytochrome P450 2D6 enzyme system is required.

DETAILED DESCRIPTION OF THE INVENTION

The active compounds of the present compositions and methods are represented by Formula III, above. Throughout this application, various references are referred to, often, although not always, within parentheses or square brackets. The disclosures of all of these publications in their entireties are hereby incorporated by reference as if written herein.

Compounds of Formula III possess a center of asymmetry at the carbon to which R is attached (C-9), thereby giving rise to two enantiomers. The present invention envisions the use of either pure enantiomer or a mixture of the two enantiomers in any proportion. Thus, the term "hydroxyrisperidone," for example, as used herein means that a particular composition contains from 100% by weight of (−)-hydroxyrisperidone to 100% by weight of (+)-hydroxyrisperidone, and all intermediate mixtures. A preferred intermediate mixture is the racemate. The registry number of racenic hydroxyrisperidone is 144598-75-4.

The term "adverse effects" includes, but is not limited to, prolonged QT effect, extrapyramidal effects such as tardive dyskinesia, orthostatic hypotension and dizziness, drowsiness, palpitations, weight gain, erectile dysfunction, rashes and rhinitis. The term is intended to encompass at least all of the adverse effects reported in risperidone-treated patients as previously described herein.

The literature describes a close resemblance in the pharmacological profiles of risperidone and its 9-hydroxy metabolite, and they have been shown to exhibit similar effects. Megens and Awouters [*Drug Development Research*, 33:399–142 (1994)], concluded that "[a]s metabolic conversion of risperidone to 9-OH-risperidone does apparently not result in any marked change in activity profile, its major consequence seems to be a prolongation of duration of action." van Beijsterveldt et al. [*Psychopharmacology*, 114:53–62 (1994)] similarly concluded that the pharmacological properties of the hydroxy metabolite are comparable to the parent compound, "both in respect of the profile of interactions with various neurotransmitters and its potency, activity, and onset and duration of action."

It has now been discovered that compounds of Formula III are superior agents for treating psychoses and other disorders in that they provide effective treatment while exhibiting fewer or less severe adverse effects than risperidone, less potential for drug-drug interactions than risperidone, as well as a more predictable dosing regimen than risperidone. Compounds of Formula III also provide more predictable elimination and clearance in elderly patients and patients with impaired renal function.

The present invention encompasses a method of treating psychoses, which comprises administering to a human in need of such therapy, an amount of a compound of Formula III, or a pharmaceutically acceptable salt thereof, which is sufficient to alleviate the symptoms of psychosis. The present invention further encompasses a method of treating diarrhea, gastro-esophageal reflux and emesis. The present invention yet further encompasses a method of treating autism, hypertension, vascular disorders, obesity, and the withdrawal symptoms associated with cessation of drinking and smoking.

Preferably, the methods of the present invention are practiced by administering a pharmaceutical composition in the form of a tablet, capsule, or liquid comprising between about 1 and 20 mg of a compound of Formula III.

Utilizing compounds of Formula III provides enhanced dosage predictability and an improved therapeutic index as compared to risperidone. In particular, the compounds exhibit less variation in the patient population between so-called extensive metabolizers and poor metabolizers than does risperidone.

The magnitude of a prophylactic or therapeutic dose of a compound of Formula III required for the acute or chronic management of disease will vary with the severity of the condition to be treated and the route of administration. The dose and perhaps the dose frequency will also vary according to the age, body weight and response of an individual patient. In general, the total daily dose range for compounds of Formula III for the conditions described herein is from about 1 mg to about 20 mg in single or, preferably, divided doses. A preferred daily dose range is about 1 mg to about 10 mg in two divided doses. In managing a particular patient, the therapy should be initiated at a lower dose, perhaps at about 1 mg, and then increased up to about 10 mg or higher, depending upon the patient's global response. It is further recommended that children and patients over 65 years of age, as well as those with impaired renal or hepatic function, initially receive low doses, and that they be titrated based upon individual response(s) and blood level(s). It may be necessary to use dosages outside the indicated ranges in some cases, as will be apparent to those skilled in the art. Further, it is noted that the clinician or treating physician will know how and when to interrupt, adjust, or terminate therapy in conjunction with individual patient response. The terms "an amount sufficient to treat psychoses," "an amount sufficient to alleviate the symptoms of emesis," "an amount sufficient to treat diarrhea," and "an amount sufficient to treat withdrawal," are encompassed by the above-described dosage amounts and dose frequency schedule.

The relative activity, potency and specificity of compounds of Formula III may be determined by a pharmacological study in animals according to the method of Nyberg et al. [*Psychopharmacology,* 119:345–348 (1995)]. The method provides an estimate of relative activity, potency and, through a measure of specificity, an estimate of therapeutic index. Although the differential metabolism among patient populations can be determined by a clinical study in humans, less expensive and time-consuming substitutes are provided by the methods of Kerr et al. [*Biochem. Pharmacol.,* 47:1969–1979 (1994)] and Karam et al. [*Drug Metab. Dispos.,*24:1081–1087 (1996)]. The potential for drug-drug interactions may be assessed clinically according to the methods of Leach et al. [*Epilepsia,* 37:1100–1106 (1996)], or in vitro according to the methods of Kerr et al.[supra] and Turner and Renton [*Can. J. Physiol. Pharmacol.,* 67:582–586 (1989)].

Any suitable route of administration may be employed for providing the patient with an effective dosage of a compound of Formula III. Suitable routes of administration may include, for example, oral, rectal, nasal, buccal, parenteral (such as, intravenous, subcutaneous, intramuscular, intrasternal, intrathecal, intrahepatic, intralesional, intracranial, intra-articular, and intra-synovial), transdermal, and the like. Due to their ease of administration, oral dosage forms, such as, for example, tablets, troches, dispersions, suspensions, solutions, capsules, soft gelatin capsules, and the like, may be preferred.

Pharmaceutical compositions of the present invention comprise a compound of Formula III, or a pharmaceutically acceptable salt thereof, as the active ingredient, and may contain a pharmaceutically acceptable carrier, as well as other therapeutic ingredients. The terms "pharmaceutically acceptable salts," and "a pharmaceutically acceptable salt thereof," refer to salts prepared from pharmaceutically acceptable non-toxic acids or bases. Salts of compounds of Formula III are more soluble than either risperidone or hydroxyrisperidone and are therefore well-suited for parenteral, and in particular, intravenous administration.

Since the hydroxy compound of Formula III is basic, salts may be prepared from pharmaceutically acceptable non-toxic acids, including both inorganic and organic acids. Suitable pharmaceutically acceptable acid addition salts of Formula III include, but are not limited to, acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like. The tartrate, hydrochloride and pamoate salts are preferred salts of the hydroxy compound.

The phosphate and sulfate compounds of Formula III are acidic, and therefore allow for the preparation of salts of bases as well as internal salts. Suitable pharmaceutically acceptable base addition salts include, but are not limited to, metallic salts made from aluminum, calcium, lithium, magnesium, potassium, sodium and zinc, as well as organic salts made from chloroprocaine, choline, N,N'-dibenzylethylenediamine, diethanolamine, ethylenediamine, lysine, meglumine (N-methylglucamine) and procaine. The N-methylglucamine salt of the phosphate compound is a preferred compound for parenteral administration, and in particular, for intravenous administration.

The compositions of the present invention may comprise, but are in no way limited to, suspensions, solutions, elixirs and solid dosage forms. Carriers, such as starches, sugars, and microcrystalline cellulose, diluents, granulating agents, lubricants, binders, disintegrating agents, and the like are suitable in the case of oral solid preparations (such as, for example, powders, capsules, soft gelatin capsules, tablets and the like). In some cases, it may be advantageous to coat oral solid dosage forms with an enteric or delayed-release coating, and such may be accomplished by standard aqueous or nonaqueous techniques. Oral dosage forms suitable for compounds of the present invention are described in U.S. Pat. Nos. 5,158,952; 5,453,425; and 5,612,346. In addition to the common dosage forms set out above, the compounds of the present invention may also be administered by controlled release formulations, which are well known in the art.

Pharmaceutical compositions of the present invention suitable for oral administration may be presented in the form of discrete units such as capsules, cachets, soft gelatin capsules, and tablets, wherein each unit contains a predetermined amount of the active ingredient, as a powder or as granules, or as a solution or a suspension in an aqueous liquid, a non-aqueous liquid, an oil-in-water emulsion, or a water-in-oil liquid emulsion. Such compositions may be prepared by any of the methods of pharmacy, any of which will typically include the step of bringing into association the active ingredient with a carrier that constitutes one or more necessary ingredients. In general, the compositions are prepared by uniformly and intimately admixing the active ingredient with liquid carriers or finely divided solid carriers or both, and then, if necessary, shaping the product into the desired presentation.

Tablets, for example, may be prepared by compression or molding, optionally, with one or more accessory ingredients. Compressed tablets may be prepared by compressing in a suitable machine an amount of the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet, or other presentation, contains between about 1 to 10 mg, and more desirably, between about 1 to 5 mg of the active ingredient.

An enteric coating, such as the polyacrylate Eudragit L® and Eudragit S® series, may be applied, preferably with an aqueous dispersion of the coating polymer. Tablets of other strengths may also be prepared by altering the ratio of active ingredient to the excipients or to the final weight of the tablet.

The invention is further defined by reference to the following examples describing in detail the preparation of compounds and compositions of the present invention. It will be apparent to those skilled in the art that many modifications, both to materials and methods, may be practiced without departing from the spirit of the invention.

Preparation of Compounds of Formula III

Compounds represented by Formula III of the present invention wherein R is —OH may be prepared as described in U.S. Pat. No. 5,158,952. Example 3 of the reference teaches a method for the preparation of (rac)-hydroxyrisperidone from 3-(2-chloroethyl)-6,7,8,9-tetrahydro-9-hydroxy-4H-pyrido[1,2-a]pyrimidin-4-one and 6-fluoro-3-(4-piperidinyl)-1,2-benzisoxazole monohydrochloride utilizing an art-known N-alkylation reaction.

Compounds represented by Formula III of the present invention wherein R is —P(O)(OH)$_2$ may be prepared by various methods. A first approach utilizes the same starting materials as the above-described preparation of hydroxyrisperidone and is based upon methods known in the art. 3-(2-chloroethyl)-6,7,8,9-tetrahydro-9-hydroxy4H-pyrido[1,2-a]pyrimidin-4-one is treated with diphenyl chlorophosphate and N,N-dimethyl-4-pyridinamine in dichloromehane according to the protocol described in Example 13 of published PCT patent application WO 95/19983. The diphenyl reaction product is then submitted to a two-step hydrolysis as described in Example 15 of that reference. The phosphate reaction product is then mixed with 6-fluoro-3-(4-piperidinyl)-1,2-benzisoxazole monohydrochloride in accordance with the N-alkylation reaction described in Example 3 of U.S. Pat. No. 5,158,952, whereby a compound of Formula III, wherein R is —P(O)(OH)$_2$ is obtained.

In accordance with a second method, the phosphate compound may be prepared from hydroxyrisperidone by treating the hydroxy compound with (1) iPr$_2$NP(OCH$_2$Ph), tetrazole; (2) t-BuOOH; and (3) Pd/C, H$_2$. In addition, the N-methylglucamine salt of the phosphate compound may be obtained by including N-methylglucamine in step (3).

Compounds of Formula III wherein R is —SO$_3$H may be prepared from hydroxyrisperidone according to the method of Laiv and Goren [*Carb. Res.*, 131 C, (1984)].

Preparation of Pharmaceutical Compositions Including a Compound of Formula III

| | |
|---|---|
| hydroxyrisperidone | 1.00 mg |
| lactose | 11.00 mg |
| corn starch | 2.85 mg |
| microcrystalline cellulose | 1.00 mg |

| -continued | |
|---|---|
| hydrogenated vegetable oil | 0.15 mg |
| Total weight per tablet | 16.00 mg |

Hydroxyrisperidone, lactose and corn starch are mixed together, water is added, and the mixture is kneaded, then dried in vacuum at 40° C. for 16 hours, ground in a mortar and passed through a 16-mesh sieve to give granules. To this is added microcrystalline cellulose and vegetable oil, and the ingredients mixed thoroughly. The resultant mixture is made up into tablets, each weighing 16 mg, on a rotary tableting machine. Tablets of other strengths may be prepared by altering the ratio of active ingredient to the excipients or to the final weight of the tablet.

What is claimed is:

1. A method of treating psychoses while avoiding the concomitant liability of side effects associated with risperidone which comprises administering to a human an amount of a compound represented by Formula III,

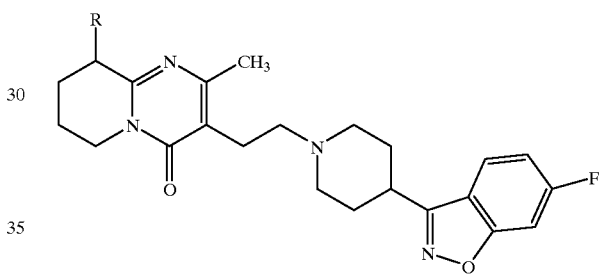

wherein R is chosen from —P(O)(OH)$_2$ and —SO$_3$H, or a pharmaceutically acceptable salt thereof, sufficient to treat psychoses but insufficient to cause said side effects.

2. A method of providing a predictable dosing regimen in the treatment of psychoses which comprises administering to a human a therapeutically effective amount of a compound represented by Formula III,

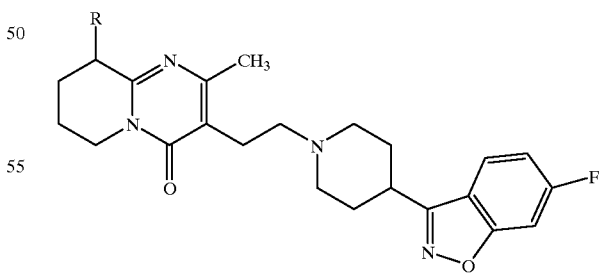

wherein R is chosen from —P(O)(OH)$_2$ and —SO$_3$H, or a pharmaceutically acceptable salt thereof.

3. A method of reducing potential for drug-drug interactions in the treatment of psychoses which comprises administering to a human a therapeutically effective amount of a compound represented by Formula III,

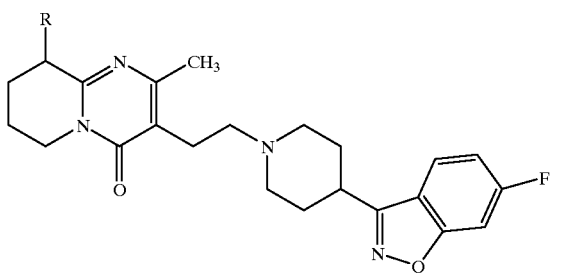

III wherein R is chosen from —P(O)(OH)$_2$ and —SO$_3$H, or a pharmaceutically acceptable salt thereof.

4. A method of suppressing emesis which comprises administering to a human a therapeutically effective amount of a compound represented by Formula III,

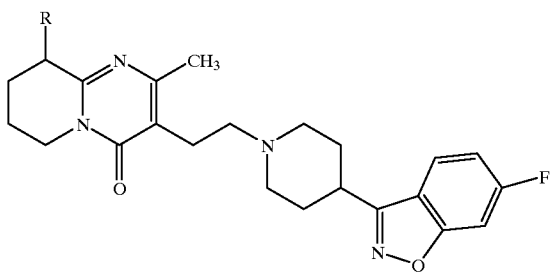

III wherein R is chosen from —P(O)(OH)$_2$ and —SO$_3$H, or a pharmaceutically acceptable salt thereof.

5. A method of treating withdrawal from alcohol, nicotine or narcotic drugs which comprises administering to a human a therapeutically effective amount of a compound represented by Formula III,

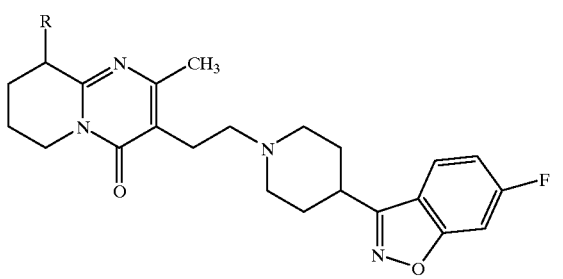

III wherein R is chosen from —P(O)(OH)$_2$ and —SO$_3$H, or a pharmaceutically acceptable salt thereof.

6. The method of claim 1 wherein R is —P(O)(OH)$_2$.

7. The method of claim 6 wherein the pharmaceutically acceptable salt thereof is the N-methylglucamine salt.

8. The method of claim 7 wherein the compound is administered intravenously.

9. A pharmaceutical composition for intravenous administration comprising the N-methylglucamine salt of a compound represented by Formula III',

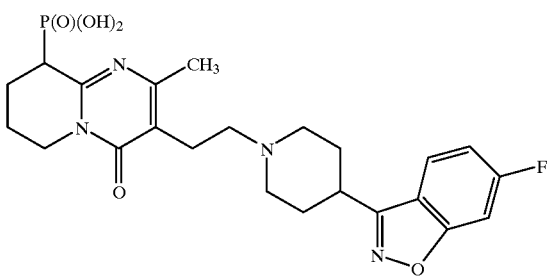

III' and a pharmaceutically acceptable carrier.

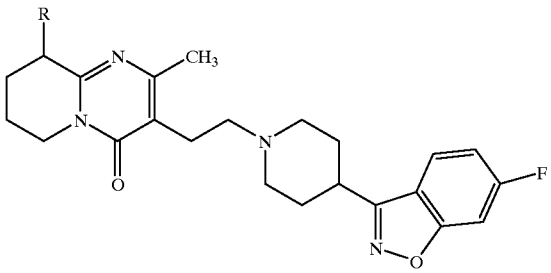

III

10. The method of claim 2 wherein R is —P(O)(OH)$_2$.
11. The method of claim 3 wherein R is —P(O)(OH)$_2$.
12. The method of claim 4 wherein R is —P(O)(OH)$_2$.
13. The method of claim 5 wherein R is —P(O)(OH)$_2$.
14. The method of claim 1 wherein R is —SO$_3$H.
15. The method of claim 2 wherein R is —SO$_3$H.
16. The method of claim 3 wherein R is —SO$_3$H.
17. The method of claim 4 wherein R is —SO$_3$H.
18. The method of claim 5 wherein R is —SO$_3$H.

* * * * *

UNITED STATES PATENT AND TRADEMARK OFFICE
CERTIFICATE OF CORRECTION

PATENT NO. : 6,342,488  
DATED : January 29, 2002  
INVENTOR(S) : Yelle

Page 1 of 1

It is certified that error appears in the above-identified patent and that said Letters Patent is hereby corrected as shown below:

<u>Column 10,</u>  
Lines 30-40, delete structrue

Signed and Sealed this

Seventh Day of May, 2002

Attest:

Attesting Officer

JAMES E. ROGAN  
*Director of the United States Patent and Trademark Office*